(12) United States Patent
Johnsson et al.

(10) Patent No.: US 8,367,361 B2
(45) Date of Patent: *Feb. 5, 2013

(54) METHODS USING O⁶-ALKYLGUANINE-DNA ALKYTRANSFERASE (75) Inventors: Kai Johnsson, Neuchatel (CH); Susanne Kindermann (née Gendreizig), Basel (CH); Antje Keppler, Heidelberg (DE)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/012,234

(22) Filed: Jan. 24, 2011

(65) Prior Publication Data

US 2011/0201514 A1    Aug. 18, 2011

Related U.S. Application Data

(63) Continuation of application No. 10/474,796, filed as application No. PCT/GB02/01636 on Apr. 5, 2002, now Pat. No. 7,939,284.

(60) Provisional application No. 60/282,766, filed on Apr. 10, 2001.

(51) Int. Cl.
| | |
|---|---|
| *C12Q 1/48* | (2006.01) |
| *C12N 15/07* | (2006.01) |
| *C12N 11/16* | (2006.01) |
| *C12P 17/12* | (2006.01) |
| *C12P 21/06* | (2006.01) |
| *G01N 33/53* | (2006.01) |
| *C12Q 1/68* | (2006.01) |

(52) U.S. Cl. ......... 435/15; 435/6.1; 435/7.12; 435/69.1; 435/122; 435/174; 435/440

(58) Field of Classification Search ..................... None
See application file for complete search history.

(56) References Cited

FOREIGN PATENT DOCUMENTS
DE    19903895 A1    8/2000
DE    019903895 A1 *  8/2000

OTHER PUBLICATIONS

Dolan et al. 1990. Depletion of mammalian O6-alkylguanine-DNA alkyltransferase activity by O6-benzylguanine provides a means to evaluate the role of this protein in protection against carcinogenic and therapeutic alkylating agents. Proc. Natl. Acad. Sci. USA, vol. 87, pp. 5368-5372.*

Moschel et al Journal of the American Chemical Society 103 5489-5494 1981.
Kreklau et al The Journal of Pharmacological and Experimental Therapeutics 297 2 524-590 2001.
Moser et al Analytical Biochemistry 281 216-222 2000.
Liem et al Nucleic Acids Research 22 9 1613-1619 1994.
Green et al Chemosphere 38 5 1085-1101 1999.
Zhukovskaya et al Nucleic Acids Research 20 22 6081-6090 1992.
Liem et al Journal Molecular Biology 231 950-959 1993.
Ishibashi et al Journal Biological Chemistry 269 10 7645-7650 1994.
Morgan et al Journal Biological Chemistry 268 26 19802-19809 1993.
Hansen et al Journal Biologial Chemistry 273 2 756-762 1998.
R. Damoiseaux, et al., "Synthesis and applications of chemical probes for human 06-alkylguainine-DNA alkytransferase", Chembiochem: A European Journal of Chemical Biology, Germany, vol. 2, No. 4, pp. 285-287, Apr. 2, 2001.
G. Vaidyanathan, et al., "Radiolabeled guanine derivatives for the in vivo mapping of 0(6)-alkylguanine-DNA alkyltransferase: 6-(4-'(18)FlFluoro-benzyloxy-9H-purin-2-ylamine and 6-(3-'(131)L!lodo-benzyloxy)-9H-purin-2-ylamine", Bioconjugate Chemistry, American Chemical Society, Washington, U.S., vol. 11, pp. 868-875, Nov. 2000.
Jerzy Olejnik, et al., "Photocleavable aminotag phosphoramidites for 5'-termini DNA/RNA labeling" Nucleic Acids Research, Oxford University Press, Surrey, GB, vol. 26, No. 15, pp. 3572-3576, Aug. 1, 1998.
N. N. Swamy, et al., "Development of an affinity-driven cross-linker: isolation of a vitamin D receptor associated factor", Bioorganic & Medicinal Chemistry Letters, Oxford, GB, vol. 10, No. 4, pp. 361-364, Feb. 2000.
D.G. Jay et al., "Chromophore-assisted laser inactivation (CALI) to elucidate cellular mechanisms of cancer", BBA Reviews on Cancer, Elsevier Science BV, Amstedam, NL. vol. 1424, No. 2-3, pp. M39-M48, Oct. 29, 1999.
Antje Keppler et al., "A general method for the covalent labeling of fusion proteins with small molecules in vivo.", Nature Biotechnology, vol. 21, No. 1, pp. 86-89, Jan. 20, 2003.

* cited by examiner

*Primary Examiner* — Jon P Weber
*Assistant Examiner* — Kailash C Srivastava
(74) *Attorney, Agent, or Firm* — New England Biolabs, Inc; Harriet M. Strimpel (57) ABSTRACT

A method of using O⁶-alkylguanine-DNA alkyltransferase (AGT) is disclosed for transferring a label from a substrate to a fusion protein comprising the AGT. This allows the detection and/or manipulating of the fusion protein, both in vitro and in vivo, by attaching molecules to the fusion proteins that introduce a new physical or chemical property to the fusion protein. Examples of such molecules are, among others, spectroscopic probes or reporter molecules, affinity tags, molecules generating reactive radicals, cross-linkers, ligands mediating protein-protein interactions or molecules suitable for the immobilisation of the fusion protein.

65 Claims, 3 Drawing Sheets

Fig. 1(B).

O6-Benzylguanine (BG)

R1: H, β-D-2'-deoxyribosyl, oligodeoxyribonucleotide or any molecule accepted by AGT R2: chemical linker label: chemical probe for detection and/or manipulation of fusion protein

METHODS USING O⁶-ALKYLGUANINE-DNA ALKYTRANSFERASE

CROSS REFERENCE

This application is a continuation application of U.S. application Ser. No. 10/474,796 filed Oct. 10, 2003, which is a §371 application of International Application No. PCT/GB02/01636 filed Apr. 5, 2002, which claims priority from U.S. Provisional Application Ser. No. 60/282,766 filed Apr. 10, 2001, herein incorporated by reference.

FIELD OF THE INVENTION

The present invention relates to methods of transferring a label from a substrate to a fusion protein comprising a protein of interest and an $O^6$-alkylguanine-DNA alkyltransferase (AGT), and in particular to methods which further comprise detecting and/or manipulating the labelled fusion protein.

BACKGROUND OF THE INVENTION

Progress in understanding complex biological systems depends on characterizing the underlying interactions of biomolecules, in particular proteins. While the DNA sequencing of an increasing number of organisms has identified their open reading frames (ORF), the possibilities to study the behaviour of the corresponding proteins in the living cell and to characterize multi-protein interactions in vivo and in vitro are limited. Most strategies that aim at realizing this objective are based on the construction of a fusion protein that, upon changes in the environment of the coupled protein, elicits a physical, physiological or chemical response. Examples include the yeast-two hybrid system, split-ubiquitin and green fluorescent protein (GFP) fusion proteins. However, all these techniques have various limitations or disadvantages.

German Patent Application No: 199 03 895 A (Kai Johnsson) describes an ELISA assay for the detection of $O^6$-alkylguanine-DNA alkyltransferase (AGT). The mutagenic and carcinogenic effects of electrophiles such as N-methyl-N-nitrosourea are mainly due to the $O^6$-alkylation of guanine in DNA. To protect themselves against DNA-alkylation, mammals and bacteria possess a protein, $O^6$-alkylguanine-DNA alkyltransferases (AGT) which repairs these lesions [Pegg et al., 1995]. AGT transfers the alkyl group in a $S_N2$ reaction to one of its own cysteines, resulting in an irreversibly alkylated enzyme. As overexpression of AGT in tumour cells enables them to acquire drug resistance, particularly to alkylating drugs such as procarbazine, dacarbazine, temozolomide and bis-2-chloroethyl-N-nitrosourea, inhibitors of AGT have been proposed for use as sensitisers in chemotherapy [Pegg et al., 1995]. DE 199 03 895 A discloses an assay for measuring levels of AGT which relies on the reaction between biotinylated $O^6$-alkylguanine-derivatives and AGT which leads to biotinylation of the AGT. This in turn allows the separation of the AGT on a streptavidin coated plate and its detection, e.g. in an ELISA assay. The assay is suggested for monitoring the level of AGT in tumour tissue, adjusting treatment using AGT inhibitors as sensitisers in chemotherapy and for use in screening for AGT inhibitors.

Damoiseaux, Keppler and Johnsson (ChemBiochem., 4: 285-287, 2001) discloses the modified $O^6$-alkylated guanine derivatives incorporated into oligodeoxyribonucleotides for use as of chemical probes for labelling AGT, again to facilitate detecting the levels of this enzyme in cancer cells to aid in research and in chemotherapy. Two types of variant AGT substrates and an assay for AGT in which it is labelled with biotin (the same as that described in DE 199 03 895 A) are disclosed. In addition, the use of these $O^6$-alkylated derivatives in the directed evolution of the AGT is suggested.

SUMMARY OF THE INVENTION

Broadly, the present invention relates to a further use of $O^6$-alkylguanine-DNA alkyltransferase (AGT) in a method of labelling, and optionally subsequently manipulating and/or detecting, a protein or peptide of interest in a system in which a fusion of the protein or peptide and AGT is contacted with a labelled substrate so that the AGT transfers the label from the substrate to the AGT fusion, thereby allowing the labelled AGT-protein fusion to be manipulated and or detected by virtue of the transferred label. This contrasts with the prior art uses of assays for measuring AGT levels in which the AGT is not present as a fusion protein.

Accordingly, in a first aspect, the present invention provides a method which comprises contacting a fusion protein comprising protein of interest and an $O^6$-alkylguanine-DNA alkyltransferase (AGT) and a substrate having a label so that the AGT transfers the label so that it is covalently bonded to the fusion protein. After transfer of the label to the fusion protein, the method may additionally involves the further step of detecting and/or manipulating the labelled fusion protein.

In one embodiment, the present invention provides a method of labelling a fusion protein comprising protein of interest and an $O^6$-alkylguanine-DNA alkyltransferase (AGT), the method comprising contacting the fusion protein with a substrate having a label so that the AGT transfers the label so that it is covalently bonded to the fusion protein.

In some embodiments, the method comprises one or more further steps, for example detecting and/or manipulating the labelled fusion protein.

In a further aspect, the present invention provides a method of detecting a fusion protein comprising protein of interest and an $O^6$-alkylguanine-DNA alkyltransferase (AGT), the method comprising contacting the fusion protein with a substrate having a label so that the AGT transfers the label so that it is covalently bonded to the fusion protein and detecting the protein construct using the label.

In a further aspect, the present invention provides a method of manipulating a fusion protein comprising protein of interest and an $O^6$-alkylguanine-DNA alkyltransferase (AGT), the method comprising contacting the fusion protein with a substrate having a label so that the AGT transfers the label so that it is covalently bonded to the fusion protein and manipulating the fusion protein using a physical and/or chemical property introduced by the label to the fusion protein.

In some embodiments of this aspect of the invention, the method may comprise detecting the protein construct using the label.

In a further aspect, the present invention provides a method of immobilising a fusion protein comprising protein of interest and an alkylguanine-DNA alkyltransferase (AGT) on a solid support, the method comprising contacting the fusion protein with a substrate having a label which is attached or attachable to a solid support, wherein the AGT transfers the label so that it is covalently bonded to the fusion protein which thereby is attached or can be subsequently attached to the solid support. In embodiments of the invention in which the label is not initially attached to the solid support, the method may involve the further step of contacting the labelled fusion protein with the solid support so that it becomes immobilised on the solid support. In preferred embodiments of this aspect of the invention, the label may be covalently attached to the solid support, either when the label is transferred or in a subsequent reaction, or may be one member of a specific binding pair, the other member of which is attached or attachable to the solid support, either covalently or by any other means (e.g. using the specific binding pair of biotin and avidin or streptavidin).

In a further aspect, the present invention provides a method to label AGT fusion proteins both in vivo as well as in vitro. The term in vivo labelling of a AGT fusion protein includes labelling in all compartments of a cell as well as of AGT fusion proteins pointing to the extracellular space. If the labelling of the AGT fusion protein is done in vivo and the protein fused to the AGT is a plasma membrane protein, the AGT part of the fusion protein can be either attached to the cytoplasmic or the extracellular side of the plasma membrane. If the labelling is done in vitro, the labelling of the fusion protein can be either performed in cell extracts or with purified or enriched forms of the AGT fusion protein.

In a further aspect, the present invention provides a method of determining the interaction of a candidate compound or library of candidate compounds and a target substance or library of target substance. Examples of compounds and substances include ligands and proteins, drugs and targets of the drug, or small molecules and proteins. In this method, the protein of interest fused to the AGT comprises a DNA binding domain of a transcription factor or an activation domain of a transcription factor, a target substance or library of target substances is linked to the other of the DNA binding domain or the activation domain of the transcription factor, and the label is a candidate compound or library of candidate compounds suspected of interacting with the target substance(s).

In preferred embodiments, the method may further comprise transferring the candidate compound or library of candidate compounds to the AGT protein fusion and contacting the AGT fusion protein(s) labelled with the candidate compounds and the target substance(s) so that the interaction of a candidate compound joined to the AGT fusion protein and a target substance activates the transcription factor. The activated transcription factor can then drive the expression of a reporter which, if the method is carried out in cells, can be detected if the expression of the reporter confers a selective advantage on the cells. In some embodiments, the method may involve one or more further steps such as detecting, isolating, identifying or characterising the candidate compound(s) or target substance(s).

In the present application, the $O^6$-alkylguanine-DNA alkyltransferase or 'AGT' has the property of transferring a label present on a substrate to one of the cysteine residues of the AGT forming part of a fusion protein. In preferred embodiments, the AGT is an $O^6$-alkylguanine-DNA alkyltransferase, for example human $O^6$-alkylguanine-DNA alkyltransferase which is described in Pegg et al 1995 and references therein. However, other alkylguanine-DNA alkyltransferases are known, e.g. murine or rat forms of the enzyme described in Roy et al., 1995, which can be employed in the present invention provided that they have the property defined above. In the present invention, $O^6$-alkylguanine-DNA alkyltransferase also includes variants of a wild-type AGT which may differ by virtue of one or more amino acid substitutions, deletions or additions, but which still retain the property of transferring a label present on a substrate to the AGT or the protein or peptide with which it forms a fusion. Other variants of AGTs may be chemically modified using techniques well known to those skilled in the art. AGT variants may be produced using protein engineering techniques known to the skilled person and/or using molecular evolution to generate and select new $O^6$-alkylguanine-DNA alkyltransferases.

In the present invention, the reference to the protein part of the fusion protein with the AGT is intended to include proteins, polypeptides and peptides of any length and both with and without secondary, tertiary or quaternary structure. Examples of applications of the present invention are provided below.

In the present invention, the labelled substrate is preferably a labelled benzylguanine substrate, and more preferably is an $O^6$-benzylguanine derivative. An example of such a derivative is an $O^6$-benzylguanine derivative that is derivatised at the 4-position of the benzyl ring with the following general formula:

wherein:
$R^1$ is a proton, a -D-2'-deoxyribosyl, or a β-D-2'-deoxyribosyl that is part of an oligodeoxyribonucleotide, preferably having a length between 2 and 99 nucleotides;
$R^2$ is a linker group, for example a flexible linker such as a substituted or unsubstituted alkyl chain, a polyethylene glycol; and
label is a molecule responsible for the detection and/or manipulation of the fusion protein as described herein.

Examples of modified $O^6$-benzylguanine derivatives suitable for use in accordance with the present invention are provided in FIG. 1. Further, the present inventors have found that the AGT can tolerate a considerable degree of flexibility in the identity of the substrate, allowing a wide range of substrates to be used with the following general formula:

wherein:
$R^1$ is a group accepted by AGT, allowing the AGT to transfer the label to the AGT-protein fusion, for example a substituted or unsubstituted alkyl chain, a substituted or unsubstituted cycloalkyl group with a ring size between three and ten carbons, a substituted or unsubstituted heterocycle with a ring size between three and ten carbons, a substituted or unsubstituted aromatic heterocycle with a ring size between three and ten carbons;
$R^2$ is a linker group, for example a flexible linker of varying length such as a substituted or unsubstituted alkyl chain or a polyethylene glycol; and
$R^3$ is a proton, a β-D-2'-deoxyribosyl, or a β-D-2'-deoxyribosyl that is part of an oligodeoxyribonucleotide, preferably having a length between 2 and 99 nucleotides; and
label is a molecule responsible for the detection and/or manipulation of the fusion protein as described herein.

The label part of the substrate can be chosen by those skilled in the art dependent on the application for which the fusion protein is intended. Examples of labels include:
(1) A spectroscopic probe such as a fluorophore, a chromophore, a magnetic probe or a contrast reagent;
(2) A radioactively labelled molecule;
(3) A molecule which is one part of a specific binding pair which is capable of specifically binding to a partner. Such specific binding pairs are well known in the art and include, for example, biotin, which can bind to avidin or streptavidin;
(4) A molecule that are suspected to interact with other biomolecules;
(5) A library of molecules that are suspected to interact with other biomolecules;
(6) A molecule which is capable of crosslinking to other biomolecules as known to those skilled in the art [Nadeau et al., 2002];
(7) A molecule which is capable of generating hydroxyl radicals upon exposure to $H_2O_2$ and ascorbate such as a tethered metal-chelate [Hori et al., 2002];
(8) A molecule which is capable of generating reactive radicals upon irradiation with light such as malachite green [Jay et al. 1999];
(9) A molecule covalently attached to a solid support, where the support may be a glass slide, a microtiter plate or any polymer in general known to those proficient in the art;
(10) A nucleic acid or a derivative thereof capable of undergoing base-pairing with its complementary strand;
(11) A lipid or other hydrophobic molecule with membrane-inserting properties.
(12) A biomolecule with desirable enzymatic, chemical or physical properties;
(13) A molecule possessing a combination of any of the properties listed above.

By way of example, embodiments of the present invention will now be described in more detail with reference to the accompanying figures.

BRIEF DESCRIPTION OF THE FIGURES

FIG. 1: A) Mechanism of $O^6$-alkylguanine-DNA alkyltransferase; B) Structure of $O^6$-benzylguanine; C) General structure of $O^6$-benzylguanine derivatives used in the examples; D) General scheme for labeling of AGT fusion proteins, X being the protein fused to AGT; E) Structures of AGT substrates used in the examples. The sequence of the oligonucleotide (22mer) is: 5'-GTGGTGGGCGCTGXAG-GCGTGG-3' where X=BG-Bt.

DETAILED DESCRIPTION

The following applications of the present invention are provided by way of examples and not limitation. The method disclosed herein is generally applicable to a range of applications and is capable of specifically and covalently labelling fusion proteins with (1) labels which are capable of sensing and inducing changes in the environment of the labelled fusion protein and/or (2) labels which aid in manipulating the fusion protein by the physical and/or chemical properties specifically introduced by the label to the fusion protein. The method disclosed herein can be used to label AGT fusion proteins both in vivo and in vitro.

Figure 1A:
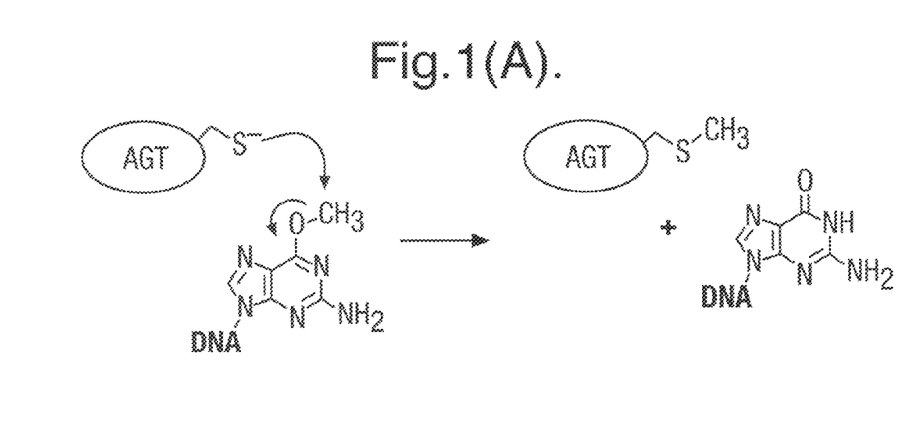
Figure 1B:
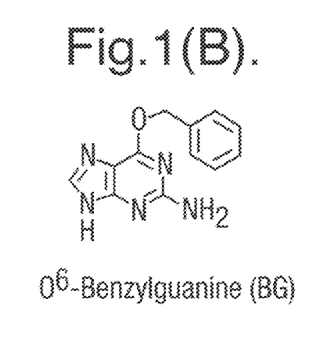
Figure 1C:
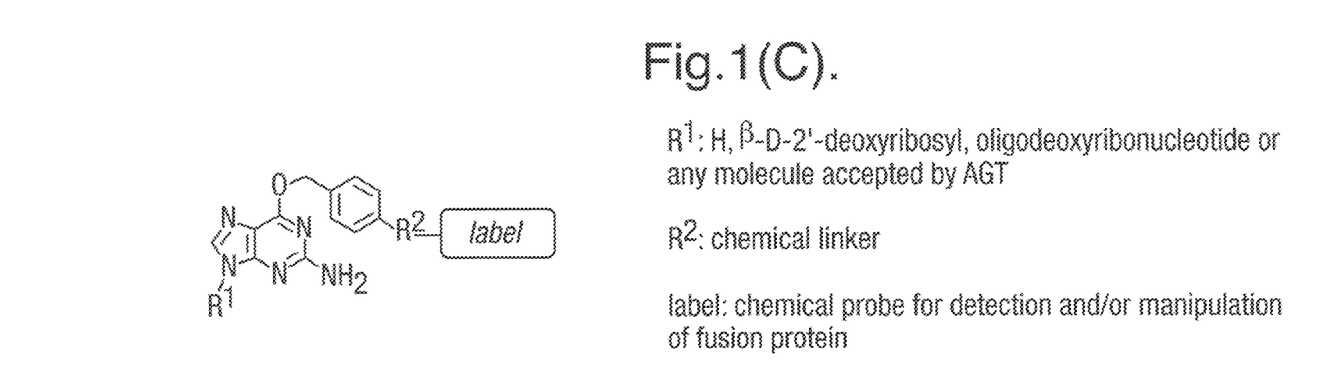
Figure 1D:
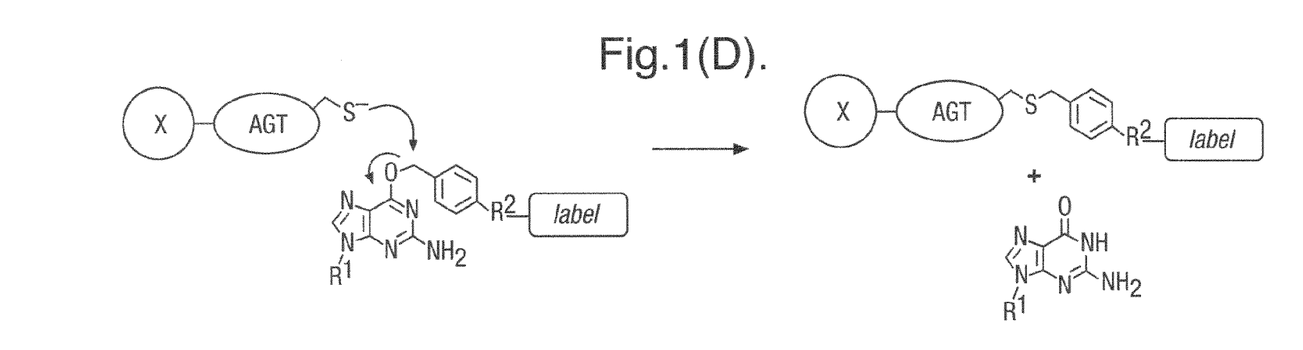

The present invention is based on the realisation that specific attachment of a label to a desired protein could be carried out by constructing a fusion protein between that protein of interest and taking advantage of the mechanism of an $O^6$-alkylguanine-DNA alkyltransferase such as human DNA repair enzyme $O^6$-alkylguanine-DNA alkyltransferase (hAGT). This enzyme irreversibly transfers the alkyl group from its substrate, $O^6$-alkylguanine-DNA, to one of its cysteine residues (FIG. 1). A substrate analogue that rapidly reacts with hAGT is $O^6$-benzylguanine, the second order rate constant being approximately $10^3$ sec$^{-1}$ M$^{-1}$ (FIG. 1). We have shown that substitutions of $O^6$-benzylguanine at the C4 of the benzyl ring do not significantly affect the reactivity of hAGT against $O^6$-benzylguanine derivatives. This enables the use of $O^6$-benzylguanine derivatives that have a label attached to the C4 of the benzyl ring to covalently and specifically attach the label AGT fusion proteins in vivo or in vitro (FIG. 1D). The labelling is independent of the nature of the fusion protein.

If the labelling is done in vivo or in cell extracts, the labelling of the endogenous AGT of the host is advantageously taken into account. If the endogenous AGT of the host does not accept $O^6$-benzylguanine derivatives or related compounds as a substrate, the labelling of the fusion protein is specific. In mammalian cells (human, murine, rat), labelling of endogenous AGT is possible. In those experiments where the simultaneous labelling of the endogenous AGT as well as of the AGT fusion problem poses a problem, previously described AGT-deficient cell lines can be used [Kaina et al. 1991]. In general, the present invention can be employed in all applications of the technique were the covalent and specific attachment of a label to a AGT fusion protein is used to monitor or influence the behaviour of the AGT fusion protein or is used to manipulate the AGT fusion protein by virtue of the introduced label. Examples of applications for the use of this technology follow.

1) The Label as a Spectroscopic Probe or Reporter Group

The use of a labelled AGT substrates, such as $O^6$-benzylguanine derivatives, where the substrate carries a detectable label which can be transferred to the AGT, such as a fluorophore, a chromophore, a magnetic probe, a radioactively labelled molecule or any other spectroscopic probe, allows the present invention to be used to specifically and covalently attach the detectable label to the AGT fusion protein, either in a cell, on the surface of a cell (in vivo) or in vitro. This allows the detection and characterization of the AGT fusion protein in vivo or in vitro. The term in vivo includes labelling in all compartments of a cell as well as of AGT fusion proteins pointing to the extracellular space. The method can be compared to the applications of the green fluorescent protein (GFP) which is also genetically fused to the protein of interest and allows its investigation in the living cell. The disadvantage of GFP and its mutants is that it is principally limited to the use of the natural occurring fluorophore.

2) The Label as a Tag to Detect and Isolate AGT Fusion Proteins

The use of AGT substrates, such as $O^6$-benzylguanine derivatives, which are labelled with an affinity tag such as biotin allows the present invention to be used to transfer an affinity tag to the AGT-protein fusion, thereby allowing the fusion protein to be bound by a binding partner of the affinity tag. By way of example, the addition of AGT substrates labelled with an affinity tag such as biotin to cells (bacterial or eukaryotic) expressing an AGT fusion protein, or to the cell extracts of such cells or to purified AGT fusion proteins, will lead to the covalent modification of the fusion protein with the affinity tag. This will then allow the isolation of the fusion protein using the interaction between the affinity tag and its binding partner, e.g. in the case of biotin, immobilized avidin or streptavidin. If the label is linked to the AGT-protein fusion via a linker containing a cleavable bond, such as a disulfide bridge, or if the linker is photocleavable, the AGT fusion protein can be released from the affinity tag after its isolation.

3) The Label as of Source of Reactive Radicals

AGT substrates, such as $O^6$-benzylguanine derivatives, can be used to introduce labels into AGT-protein fusions which are capable of generating reactive radicals, such as hydroxyl radicals, upon exposure to an external stimuli. The generated radicals can then inactivate the AGT fusion proteins as well as those proteins that are in close proximity of the AGT fusion protein, allowing the study the role of these proteins. Examples of such labels are tethered metal-chelate complexes that produce hydroxyl radicals upon exposure to $H_2O_2$ and ascorbate, and chromophores such as malachite green that produce hydroxyl radicals upon laser irradiation. The use of chromophores and lasers to generate hydroxyl radicals is also known in the art as chromophore assisted laser induced inactivation (CALI)[Jay et al. 1998]. CALI is a method that is used to specifically inactivate certain proteins within a cell in a time-controlled and spatially-resolved manner and which is based upon the spatial neighbourhood of a chromophore and a protein. Upon laser irradiation the chromophore generates hydroxyl radicals, which inactivate all proteins within and only within about 0.1 nm of the chromophore. So far, the chromophore is brought in the spatial neighbourhood of the protein of interest by microinjecting chromophore-labelled antibodies specific to the protein of interest. In the present invention, labelling AGT fusion proteins with chromophores such as malachite green and subsequent laser irradiation would allow to inactivate the AGT fusion protein as well those proteins that interact with the AGT fusion protein in a time-controlled and spatially-resolved manner. The method can be applied both in vivo or in vitro.

In a similar manner, AGT fusion proteins can be labelled with tethered metal-chelates and the AGT fusion protein and those proteins that interact with the AGT fusion protein can be inactivated in a specific manner upon exposure to $H_2O_2$ and ascorbate. The method can not only be used to study the function of an AGT fusion protein or those that are in close proximity of the AGT fusion protein, but also to identify those proteins that are in close proximity of a AGT fusion protein. Here, proteins which are in close proximity of the AGT fusion protein can be identified as such by either detecting fragments of that protein by a specific antibody, by the disappearance of those proteins on a high-resolution 2D-electrophoresis gels or by identification of the cleaved protein fragments via separation and sequencing techniques such as mass spectrometry or protein sequencing by N-terminal degradation.

4) The Label as a Ligand Mediating Protein-protein Interactions

The use of labelled AGT substrates, such as $O^6$-benzylguanine derivatives can be used to transfer a ligand to the AGT-protein fusion. This allows binding partners of the ligand, such as proteins, to bind to the AGT-protein fusion. For example, where the label is a ligand which is capable of binding to a binding partner, contacting such a substrate with a AGT fusion protein will lead to specific attachment of the ligand to the fusion protein. If the ligand binds to another protein Y and the dimerization of the protein Y with the labelled AGT fusion protein leads to a biological function or a measurable signal, the biological function or the measured signal depends on the addition of the AGT substrate carrying the label. A specific example would be the use of AGT substrates and AGT fusion protein in the so-called three-hybrid system described by Ho et al., 1996, to regulate gene expression with small molecules. In this case, AGT is fused to the DNA-binding domain of a transcription factor. A protein Y, such as FKBP that binds a ligand, such as FK506, is fused to the activation domain of a transcription factor. Supplying the cells with the AGT substrate that carries the ligand, in this example FK506, will lead to the formation of a functional transcription factor and gene expression.

5) The Label as a Drug or Biological Active Molecule Whose Target is Unknown

The use of $O^6$-benzylguanine derivatives or related AGT substrates that carry a label and where the label is a drug or a biological active small molecule that binds to an yet unidentified protein Y. Here the goal would be to identify the target protein Y of the biological active molecule. In this case, AGT is fused to the DNA-binding domain of a transcription factor. A cDNA library of the organism which expresses the unknown target protein Y is fused to the activation domain of a transcription factor. Adding the $O^6$-benzylguanine derivatives or related AGT substrate that carry a label and where the label is the drug or the biological active small molecule will lead to the formation of a functional transcription factor and gene expression only in the case where this molecule binds to its target protein Y present in the cDNA library and fused to the activation domain. If gene expression is coupled to a selective advantage, the corresponding host carrying the plasmid with the target gene Y of the drug or bioactive molecule can be identified.

6) The Label as a Library of Small Molecules to Identify Molecules that Bind to the Protein Y The use of $O^6$-benzylguanine or related AGT substrates that carry a label and where the label is a library of chemical molecules: Here the goal would be to identify small molecules that bind to a protein Y under in vivo conditions, which might be a potential drug target. In this case, AGT is fused to the DNA-binding domain of a transcription factor. The target protein Y is fused to the activation domain of a transcription factor. Adding a library of small molecules attached as label to a $O^6$-benzylguanine derivative will lead to the formation of a functional transcription factor and gene expression only in the case where the label (i.e. the small molecule) binds to its target protein Y fused to the activation domain. If gene expression is coupled to a selective advantage, those molecules of the library leading to the growth of the host can be identified.

7) The Use of BG Derivatives to Immobilize AGT Fusion Proteins and/or to Create Protein Arrays of AGT Fusion Proteins The use of $O^6$-benzylguanine derivatives or related AGT substrates carrying a label and where the label is covalently attached to the surface of a carrier or where the label is a molecule that can be bound non-covalently by another molecule that is itself attached to the surface. An example for the latter approach is where the label is biotin and the molecule attached to the surface is streptavidin or avidin. Possible examples for a carrier would be either a glass side, a microtiter plate or any functionalized polymer. The immobilization of the AGT substrate via its label allows the subsequent immobilization of a AGT fusion protein on the carrier by the transfer of the label to the fusion protein. Spotting (different) AGT fusion proteins in a spatially resolved manner on the carrier allows the creation of protein arrays.

8) The Label as a Cross-linker to Detect Proteins that Interact with the AGT Fusion Protein The use of $O^6$-benzylguanine derivatives or related AGT substrates which carry a label and where the label is a molecule that can cross-link to other proteins. Examples of such cross-linkers are molecules containing functional groups such as maleimides, active esters or azides and others known to those proficient in the art and described in Nadeau et al., 2002. Contacting such AGT substrates with AGT fusion proteins that interact with other proteins (in vivo or in vitro) can lead to the covalent cross-linking of the AGT fusion protein with its interacting protein via the label. This allows the identification of the protein interacting with the AGT fusion protein.

EXAMPLES

The following examples are set forth so as to provide those of ordinary skill in the art with a complete disclosure and description of how to practice the invention, and are not intended to limit the scope of the invention.

Example A

Covalent Labelling of AGT Fusion Proteins in *E. Coli*

Figure 2:
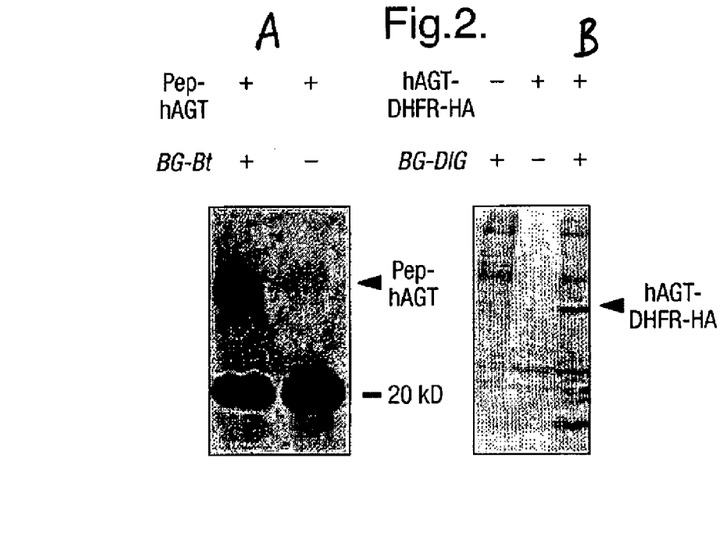
FIG. 2: Western blots after labelling of AGT fusion proteins in vivo. A) Western-Blot of total cell extract of *E. coli* expressing Pep-hAGT with and without BG-Bt in the medium. A streptavidin-peroxidase conjugate is used to detect biotinylated proteins. The band at 20 kD corresponds to a protein that is biotinylated in *E. coli* in the absence of BG-Bt. B) Western-Blot of total cell extract of yeast expressing a hAGT-DHFR-HA fusion protein with and without BG-DIG in the medium. An anti digoxigenin-peroxidase conjugate is used to detect digoxigenin-labelled proteins.
Figure 3:
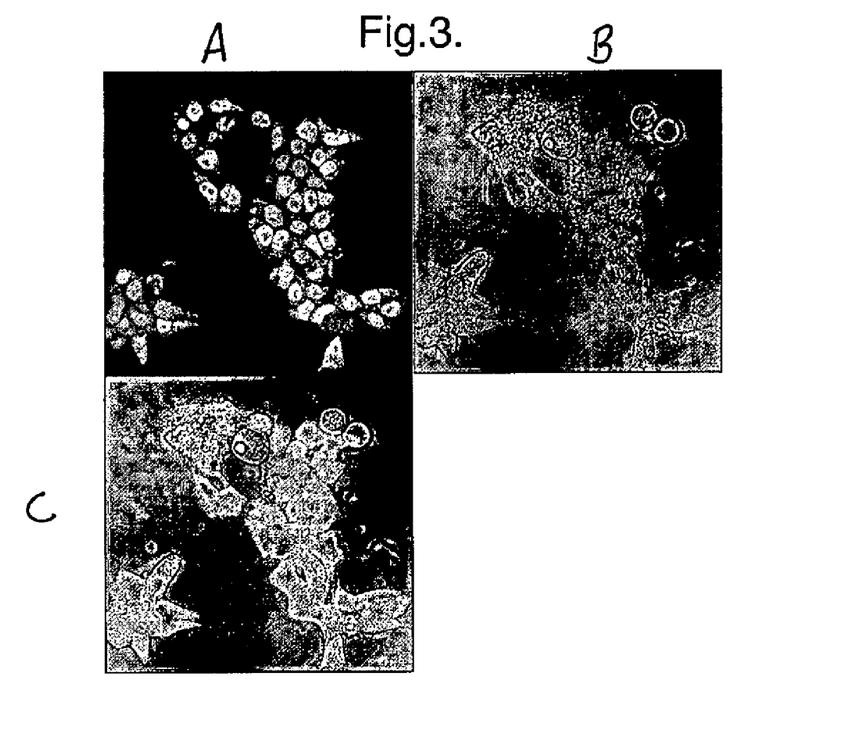
FIG. 3: HEK 293 cells incubated with BG-AcFc and analyzed by fluorescence and light microscopy. (A) shows that the fluorescence accumulates in the nucleus of the cell. (B) shows the location of hAGT in the nucleus by light microscopy [also see Ali et al., 1998]. (C) is an overlay of the images obtained from fluorescence and light microscopy.

The following example, the labelling of Pep-hAGT in *E. Coli* using BG-Bt, demonstrates the feasibility of covalently labelling hAGT fusion proteins in *E. coli*. The sequence of the peptide fused to the N-terminus of hAGT (yielding Pep-hAGT) is (in single letter code) MHHHHHHSSA followed by the first amino acid of hAGT, a methionine. Liquid cultures of XL-1 Blue *E. coli* cells containing a pET-15b (Novagen) based expression vector encoding hAGT with an N-terminal fusion peptide, i.e. Pep-hAGT, were grown to an optical density $OD_{600nm}$ of 0.6. Expression of Pep-hAGT was induced by adding IPTG to a final concentration of 1 mM. At the same time BG-Bt was added to a final concentration of 10 µM and the bacteria were incubated for 2 h at 37° C. Cells were harvested by centrifugation and the pellet washed twice to remove access BG-Bt. A re-suspended aliquot of cells was analysed by Western Blotting. Biotinylated proteins were detected using a streptavidin-peroxidase conjugate (NEN) and a chemiluminescent peroxidase substrate (Renaissance reagent plus, NEN) (FIG. 2).

Example B

Covalent Labelling of AGT Fusion Proteins in Yeast

The following example demonstrates the feasibility of covalently labelling hAGT fusion proteins in yeast. Here, a hAGT-DHFR-HA fusion protein is biotinylation in yeast using BG-Bt. The fusion protein is constructed on the DNA level using standard molecular biology procedures. In short, the stop codon of hAGT is replaced by codons for the amino acids RSGI, which are then followed by the codon for the first amino acid of DHFR from mouse, a Met [Nunberg et al., 1980]. The codons for the linker between hAGT and DHFR also encode for a Bgl II site, its DNA sequence being AGATCT. To construct the fusion between DHFR and the HA tag, the stop codon of DHFR is replaced by a codon for the first amino acid of the HA-tag [Kolodziej, 1991]. The HA-tag is followed by a stop codon. A culture of L40 yeast cells, containing the expression vector p314AK1 in which the hAGT-DHFR-HA protein is under control of the $p_{cup1}$ promoter, was grown to an $OD_{600}$ of 0.6. Expression of hAGT-DHFR-HA was induced by adding $CuSO_4$ to a concentration of 100 µM and BG-Bt was simultaneously added to a concentration of 10 µM. Aliquots were taken after 2.5 h and 5 h and cells harvested by centrifugation. The pellet was washed twice to remove remaining BG-Bt. After lysis of the yeast cells by freeze/thaw cycling the cell extract was analysed for the presence of biotinylated hAGT-DHFR-HA fusion protein using an ELISA. In short, the biotinylated hAGT-DHFR-HA was immobilized in streptavidin-coated microtiter wells and detected by using an antiHA-antibody (Babco) as a primary and an antimouse-HRP conjugate (Sigma) as a secondary antibody (FIG. 1) [Kolodziej, 1991]. The ELISA was developed using the peroxidase substrate ABTS and the signal (absorbance) measured at $OD_{405nm}$. The signal for the in vivo biotinylated hAGT-DHFR-HA fusion protein was at least fivefold above background. The background signal was defined as the $OD_{405nm}$ of cell lysates obtained from cells treated exactly as above but omitting the addition of BG-Bt.

Example C

Covalent Labelling of hAGT Fusion Proteins in Yeast

The following example demonstrates the feasibility of covalently labelling hAGT fusion proteins in yeast. Here, the hAGT-DHFR-HA fusion protein is labelled with digoxigenin in yeast using BG-DIG. The construction of the hAGT-DHFR-HA fusion is described in example B. A culture of L40 yeast cells containing the expression vector p314AK1 in which the gene of a hAGT-DHFR fusion protein is under control of the $p_{cup1}$ promoter was grown to an $OD_{600nm}$ of 1.2. Expression of the hAGT-DHFR fusion protein was induced by adding $CuSO_4$ to a concentration of 100 µM and BG-DIG was simultaneously added to a concentration of 20 µM. After 2 h cells from 1 ml of shake-flask culture were harvested by centrifugation. The pellet was washed three times with medium to remove remaining BG-DIG. After lysis of the yeast cells by freeze/thaw cycling the cell extract was analysed for the presence of digoxigenated hAGT-DHFR fusion protein by Western blotting. Digoxigenated proteins were detected using an anti-digoxigenin-peroxidase conjugate (Roche) and a chemiluminescent peroxidase substrate (Renaissance reagent plus, NEN) (FIG. 2).

Example D

Covalent Labelling of hAGT Fusion Proteins in Human Cell Lines

The following example demonstrates the feasibility of labelling AGT fusion proteins in mammalian cells. Here, endogenous hAGT in human cells (HEK 293) is labelled with fluoresceine using BG-AcFc. HEK 293 cells were incubated with 5 µM BG-AcFc in PBS for 5 min. The acetylated fluoresceine derivative BG-AcFc is cell-permeable and non-fluorescent but can be expected to be hydrolysed rapidly within the cell to yield the fluorescent BG-Fc. The cells were then washed by changing the PBS to remove any access substrate BG-AcFc and incubated in PBS for 20 min. Images were then taken with a confocal fluorescence microscope (Ext. 492 nm; Em. 510 nm). As a control experiment, the HEK 293 cells were treated as above but incubated prior to addition of BG-AcFc overnight with $O^6$-benzylguanine (1 µM). This should inactivate the endogenous hAGT and therefore prevent the accumulation of the fluorescence in the nucleus. As expected, no accumulation of fluorescence in the nucleus was observed when the cells were preincubated with $O^6$-benzylguanine. To independently confirm that the hAGT accepts BG-Fc as a substrate, recombinant Pep-hAGT (10 µM, as described in example A was incubated with 100 µM BG-Fc at 25° C. in 50 mM Tris-Cl, 10 mM DTT, 1 mM EDTA, 200 µg/ml BSA, 10% Glycerol, pH 7.4 for 10 minutes, followed by addition of 900 µl PBS (phosphate buffered saline: 137 mM NaCl, 2.7 mM KCl, 10 mM $Na_2HPO_4$, 1.8 mM $KH_2PO_4$, pH 7.4). Separation of excess substrate BG-Fc was achieved by gel filtration on a NAP-10 Column (Pharmacia) according to the supplier's instruction. The Pep-hAGT was then characterized in a standard fluorescence spectrophotometer. The sample was excited at 222, 238 and 490 nm, respectively and showed maximal emission at a wavelength of 523 nm, verifying that the protein was labelled with fluoresceine. A solution of 20 nM BG-Fc in PBS was measured as reference. The substrate's emission wavelength is 519 nm (excitation at 237, 323 and 490 nm respectively).

Example E

Covalent Labelling of AGT Fusion Proteins in Cell Extracts

To demonstrate that fusion proteins with AGT can be directly labelled and manipulated (here immobilized) in cell extracts the following N- and C-terminal fusion proteins with hAGT proteins were constructed via standard molecular cloning procedures and cloned into a yeast expression vector:

(i) V5-NLS-B42-hAGT, where V5 stands for V5 epitope, NLS for SV40 large T antigen nuclear localization sequence and B42 stands for an artificial transcriptional activator B42 [Ma et al. 1987]. The last codon of the B42 transactivation domain is followed by the 21 amino acid sequence ASKKGTELGSTTSNGRQCAGIL. The last three codons include a Eco RI site for the C-terminal cloning of the hAGT to B42. A Not I site is the C-terminal restriction site for the hAGT, whose sequence includes a stop codon;

(ii) hAGT-HA-Ura3, where Ura3 stands for the yeast enzyme orotic acid decarboxylase and HA stands for the Ha epitope. Here, the stop codon for the hAGT is replaced by RS linker followed by the first amino acid of the HA-tag. The HA-tag is directly followed by the Ura3 gene;

(iii) hAGT-DHFR-HA, where DHFR stands for the mouse dihydrofolate reductase and HA stands for the Ha epitope. Construction see example B; and (iv) SSN6-hAGT, where SSN6 stands for a yeast repressor of DNA transcription [Schultz et al. 1987]. Here, the stop codon of hAGT is replaced by codons for the amino acids RSGSG, which are then followed by the codon for the first amino acid of SSN6 of yeast, a methionine.

The expression of all genes were controlled by the $p_{CUP1}$ promoter. L40 yeast cells containing an expression vector encoding for one of the fusion protein were grown to an OD of 0.6 and expression of the fusion protein was induced by adding $CuSO_4$ to a concentration of 100 µM. Aliquots (2 ml) were taken after 5 h and cells harvested by centrifugation. After lysis of the cells by freeze/thaw cycling the yeast extract was incubated with BG-Bt-oligo (10 pmol) for 20 min at room temperature, leading to biotinylation of the fusion protein. Subsequently, the suspension was transferred into a streptavidin-coated microtiter plates (Roche molecular biochemicals) and incubated for 1 h. After extensive washing of the well with PBS, the immobilized fusion protein was detected using either an antiHA-antibody (Babco) or an anti-hAGT-antibody (in the case of the SSN6-hAGT fusion protein) as a primary and an antimouse-peroxidase conjugate (Sigma, #A4416) as a secondary antibody and subsequent incubation with the peroxidase substrate ABTS using standard biochemical procedures. In all cases, the signal which was measured as the $OD_{405nm}$ was at least five-fold above background. Background was measured for each fusion protein by omitting the addition of BG-Bt-oligo to the cell extracts.

References

All references cited herein are expressly incorporated by reference. The references are in alphabetic order.

R B Ali et al., Molecular and Cellular Biology, 18, 1660-1669. (1998)

R Damoiseaux, A Keppler and K Johnsson, *ChemBiochem*, 4, 285-287 (2001)

S N Ho et al. *Nature* 382, 822-6 (1996)

R Hori and N Baichoo in *Protein-Protein interactions: a molecular cloning manual*; Ed. E Golemis, Cold Spring Harbor Laboratory Press; pp. 288-311 (2002)

D G Jay and T Sakurai *Biochim. Biophys. Acta* M39-48 (1999)

Kaina et al. *Carcinogenesis* 12, 1857-67 1991.

P A Kolodziej and R A Young *Methods Enzymol.* 194, 508-19, (1991)

J Ma, M Ptashne *Cell* 51, 113-9, (1987)

O W Nadeau and G M Carlson in *Protein-Protein interactions: a molecular cloning manual*; Ed. E Golemis, Cold Spring Harbor Laboratory Press; pp. 75-92 (2002)

J H Nunberg et al., Cell 19, 355-364 (1980).

A E Pegg et al., *Prog Nucleic Acid Res Mol. Biol.* 51, 167-223 (1995)

J Schultz, M Carlson *Mol Cell Biol* 7, 3637-45, (1987)

The invention claimed is:

1. A method which comprises contacting a fusion protein comprising protein of interest and an $O^6$-alkylguanine-DNA alkyltransferase (AGT) and a substrate having a label so that the AGT transfers the label so that it becomes covalently bonded to the fusion protein.

2. The method according to claim 1, further comprising detecting the fusion protein using the label.

3. The method according to claim 2 which comprises detecting the labelled fusion protein in an in vitro system.

4. The method according to claim 3, wherein in the in vitro system, the labelling is carried out in cell extracts or with purified or enriched forms of the fusion protein.

5. The method according to claim 2, comprising detecting the labelled fusion protein in an in vivo system.

6. The method of claim 5, wherein the in vivo system is cells.

7. The method of claim 6, further comprising the initial step of transforming the cells with an expression vector comprising nucleic acid encoding the fusion protein linked to control sequences to direct its expression.

8. The method according to claim 1, further comprising manipulating the labelled fusion protein using a property introduced by the label to the fusion protein.

9. The method according to claim 1, wherein the protein of interest is fused to the N- or the C-terminus of the AGT.

10. The method according to claim 1, wherein the $O^6$-alkylguanine-DNA alkyltransferase is human $O^6$-alkylguanine-DNA alkyltransferase.

11. The method according to claim 1, wherein the $O^6$-alkylguanine-DNA alkyltransferase is murine or rat $O^6$-alkylguanine-DNA alkyltransferase.

12. The method according to claim 1, wherein the $O^6$-alkylguanine-DNA alkyltransferase is a mutant $O^6$-alkylguanine-DNA alkyltransferase having an amino acid sequence differing from human, rat or murine $O^6$-alkylguanine-DNA alkyltransferase by one or more amino acid substitutions, deletions or additions, but which retains the property of transferring a label present on a substrate to the AGT-protein fusion.

13. The method according to claim 1, wherein the label becomes covalently bonded to a cysteine residue of the fusion protein.

14. The method according to claim 1, wherein the labelled substrate is incorporated into a nucleic acid molecule.

15. The method according to claim 14, wherein the nucleic acid molecule is an oligonucleotide between 2 and 99 nucleotides in length.

16. The method according to claim 1, wherein the labelled substrate is a benzyl guanine substrate.

17. The method according to claim 16, wherein the benzyl guanine substrate is substituted with the label at position C4 of the benzyl ring.

18. The method according to claim 16, wherein the labelled benzyl guanine substrate is represented by the general formula:

wherein:
R¹ is a proton, a β-D-2'-deoxyribosyl or a β-D-2'-deoxyribosyl that is part of an oligodeoxyribonucleotide;
R² is a linker group; and
label represents a group for use in detecting and/or manipulating the fusion protein.

19. The method according to claim 18, wherein the linker group R² is a substituted or unsubstituted alkyl chain or a polyethylene glycol.

20. The method according to claim 18, wherein the labelled benzyl guanine substrate is represented by the general formula:

wherein:
R¹ is a group accepted by AGT allowing the AGT to transfer the label to the protein fusion;
R² is a linker group;
R³ is a proton, a β-D-2'-deoxyribosyl, or a β-D-2'-deoxyribosyl that is part of an oligodeoxyribonucleotide; and
label represents a group for use in detecting and/or manipulating the fusion protein.

21. The method according to claim 20, wherein R¹ is a substituted or unsubstituted alkyl chain, a substituted or unsubstituted cycloalkyl group with a ring size between three and ten carbons, a substituted or unsubstituted heterocycle with a ring size between three and ten carbons, or a substituted or unsubstituted aromatic heterocycle with a ring size between three and ten carbons.

22. The method according to claim 20, wherein the linker group R² is a substituted or unsubstituted alkyl chain or a polyethylene glycol.

23. The method according to claim 18, wherein the oligodeoxyribonucleotide has a length between 2 and 99 nucleotides.

24. The method according to claim 1, wherein the label is one or more of a spectroscopic probe, an affinity tag, a first member of a specific binding pair which is capable of specifically binding to the second member of the specific binding pair, a molecule which is capable of generating reactive radicals, a molecule which is a solid phase or is attached to a solid phase or is attachable to solid phase, a candidate compound or library of candidate compounds, a molecule which is capable of crosslinking to other biomolecules, a nucleic acid or a derivative thereof capable of undergoing base-pairing with its complementary strand, a lipid, or a hydrophobic molecule with membrane-inserting properties.

25. The method according to claim 24, wherein the spectroscopic probe is a fluorophore, a dye or a contrast reagent, a radioactively labelled molecule or a magnetic probe.

26. The method according to claim 24, wherein the spectroscopic probe is employed to detect or characterise the fusion protein in vitro or in vivo.

27. The method according to claim 24, wherein the affinity tag is biotin, avidin or streptavidin.

28. The method according to claim 24, wherein the affinity tag is linked to the fusion protein via a cleavable linker so that the fusion protein can be released from the affinity tag.

29. The method according to claim 24, wherein the affinity tag is linked to the fusion protein via a photocleavable linker so that the fusion protein can be released from the affinity tag.

30. The method according claim 1, further comprising immobilising the fusion protein by contacting the fusion protein with a labelled substrate which is attached or attachable to a solid support, wherein the AGT transfers the label so that it becomes covalently bonded to the fusion protein and the labelled fusion protein is thereby attached or can be subsequently attached to the solid support.

31. The method according to claim 30, wherein the label is not initially attached to the solid support, and the method comprises the further step of contacting the labelled fusion protein with the solid support so that it becomes immobilised on the solid support.

32. The method according to claim 30, wherein the label is one member of a specific binding pair, the other member of which is attached or attachable to the solid support.

33. The method according to claim 32, wherein the specific binding pair are biotin and avidin or streptavidin.

34. The method according to claim 30, wherein the label is covalently attached to the solid support by the transfer of the label or in a subsequent reaction.

35. The method according to claim 30, wherein the label is linked to the fusion protein via a cleavable linker so that the fusion protein can be released from the label after immobilisation on the solid support.

36. The method according to claim 30, wherein the label is linked to the fusion protein via a photocleavable linker so that the fusion protein can be released from the label after immobilisation on the solid support.

37. The method according to claim 30, wherein the method comprises immobilising a plurality of proteins of interest on a solid support.

38. The method according to claim 37, wherein the proteins of interest are immobilised on the solid support in an array.

39. The method of claim 38, wherein the array comprises a plurality of spatially resolved locations.

40. The method according to claim 30, wherein the solid support comprises a glass or a polymer.

41. The method according to claim 24, wherein the molecule which is capable of generating reactive radicals generates reactive hydroxyl radicals.

42. The method according to claim 41, wherein the molecule capable of generating reactive hydroxyl radicals is a tethered metal chelate which generates the radicals on exposure to $H_2O_2$ and ascorbate.

43. The method according to claim 41, wherein the molecule capable of generating reactive hydroxyl radicals generates the radicals on irradiation with light.

44. The method according to claim 43, wherein the molecule capable of generating reactive hydroxyl radicals is malachite green.

45. The method according to claim 24, wherein the radicals inactivate the fusion protein or a further protein located in proximity to the fusion protein.

46. The method according to claim 41, wherein the radicals generate fragments of the protein or further proteins located in the proximity of the fusion protein.

47. The method according to the claim 46, wherein the generation of the fragments are employed in the identification of the proteins in close proximity of the fusion protein.

48. The method according to claim 45, wherein the inactivation of the protein or further protein employs chromophore assisted laser induced inactivation (CALI).

49. The method according to claim 24, wherein the label is a first member of a specific binding pair.

50. The method according to claim 49, further comprising contacting the fusion protein with molecule comprising the second member of the specific binding pair.

51. The method according to claim 49, wherein the interaction or binding of the first and second members of the specific binding pair generates a detectable result.

52. The method according to claim 49, wherein the first and second members of the specific binding pair are a first and second protein, an antibody and antigen, an enzyme and substrate or a ligand and receptor.

53. The method according to claim 1, wherein the protein of interest fused to the AGT comprises a DNA binding domain of a transcription factor or an activation domain of a transcription factor, a target substance or library of target substances is linked to the other of the DNA binding domain or the activation domain of the transcription factor, and the label is a candidate compound or library of candidate compounds suspected of interacting with the target substance(s).

54. The method of claim 53, wherein the candidate compound or library of candidate compounds and the target substance or library of target substance are selected from a ligand and a protein, a drug and a target of the drug, a small molecule and a protein and an enzyme and its substrate or an inhibitor.

55. The method according to claim 53, comprising transferring the candidate compound or library of candidate compounds to the AGT protein fusion.

56. The method according to claim 55, further comprising contacting the AGT fusion protein(s) labelled with the candidate compounds and the target substance(s) so that the interaction of a candidate compound joined to the AGT fusion protein and a target substance reconstitutes and activates the transcription factor.

57. The method according to claim 56, wherein the activated transcription factor drives the expression of a reporter.

58. The method according to claim 57, wherein the reporter is a protein, an enzyme or an nucleic acid whose activity leads to a measurable signal.

59. The method according to claim 53, wherein the method is carried out in cells and expression of the reporter confers a selective advantage on the cells.

60. The method according to claim 53, further comprising isolating the AGT fusion protein and/or a target substances that interacts with the AGT protein fusion.

61. The method according to claim 53, further comprising detecting and/or identifying a candidate compound interacting with a target substance.

62. The method according to claim 24, wherein the label is capable of cross-linking proteins.

63. The method according to claim 62, wherein the cross-linking label comprises a maleimide group, an ester group or an azide group.

64. The method according to claim 62, comprising contacting the fusion protein with a candidate protein binding partner and reacting the cross-linking label so that interacting fusion proteins and candidate proteins become covalently linked together.

65. The method according to claim 62, further comprising detecting and/or identifying the crosslinked fusion protein and/or candidate protein.

* * * * *

SEQUENCE LISTING

<160> NUMBER OF SEQ ID NOS: 3

<210> SEQ ID NO 1
<211> LENGTH: 22
<212> TYPE: DNA

-continued

Figure 1E:
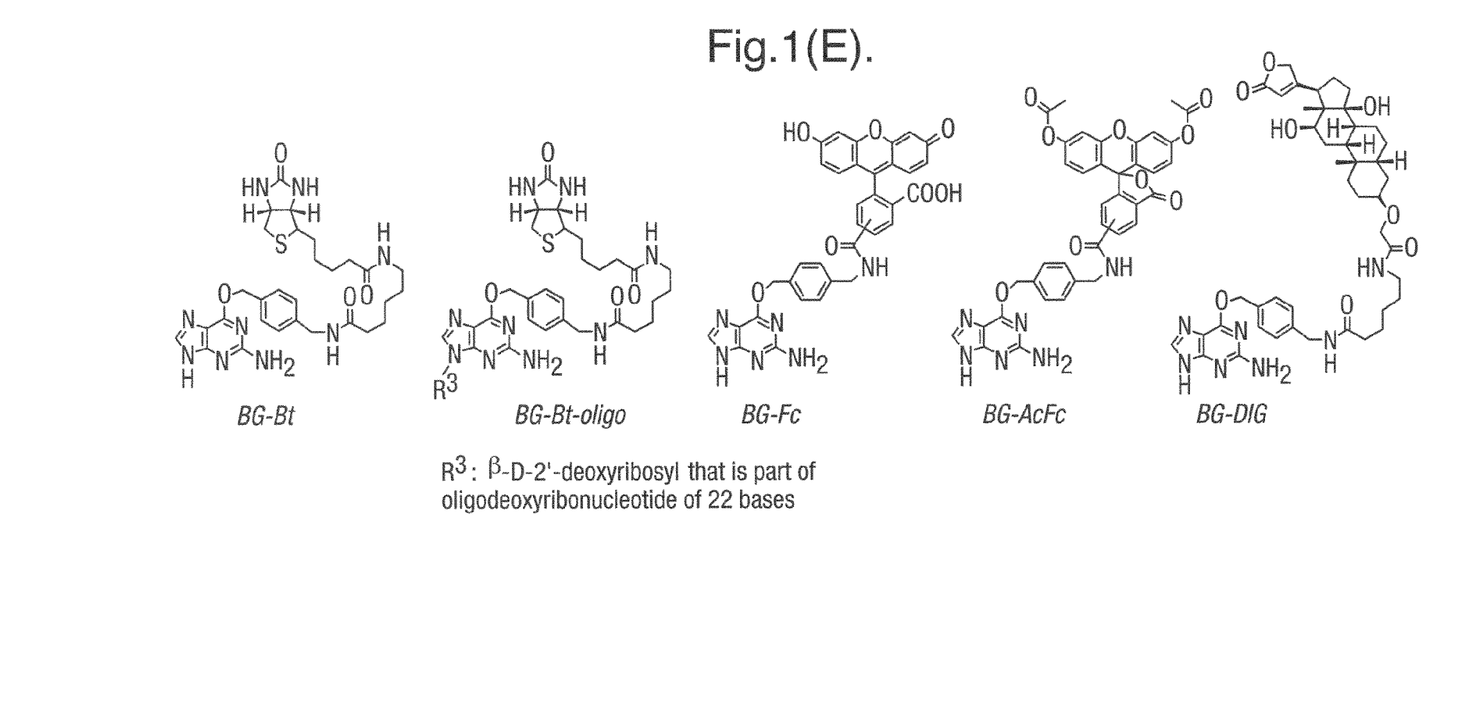

```
<213> ORGANISM: Artificial sequence
<220> FEATURE:
<223> OTHER INFORMATION: Fig 1E 22mer oligo part of R3
<220> FEATURE:
<221> NAME/KEY: misc_feature
<222> LOCATION: (14)..(14)
<223> OTHER INFORMATION: BG-BT

<400> SEQUENCE: 1
gtggtgggcg ctgnaggcgt gg                                           22

<210> SEQ ID NO 2
<211> LENGTH: 10
<212> TYPE: PRT
<213> ORGANISM: Artificial Sequence
<220> FEATURE:
<223> OTHER INFORMATION: Example A peptide Pep fused to hAGT

<400> SEQUENCE: 2

Met His His His His His His Ser Ser Ala
1               5                   10

<210> SEQ ID NO 3
<211> LENGTH: 22
<212> TYPE: PRT
<213> ORGANISM: Artificial Sequence
<220> FEATURE:
<223> OTHER INFORMATION: Example E 22 amino acids connecting B42
      activation domain to hAGT

<400> SEQUENCE: 3

Ala Ser Lys Lys Gly Thr Glu Leu Gly Ser Thr Thr Ser Asn Gly Arg
1               5                   10                  15

Gln Cys Ala Gly Ile Leu
            20
```